(12) United States Patent
Gangl et al.

(10) Patent No.: US 6,817,554 B2
(45) Date of Patent: Nov. 16, 2004

(54) FLUID NANOSPLITTER DEVICE

(75) Inventors: Eric Gangl, Somerville, MA (US); Paul Vouros, Concord, MA (US)

(73) Assignee: Northeastern University, Boston, MA (US)

(*) Notice: Subject to any disclaimer, the term of this patent is extended or adjusted under 35 U.S.C. 154(b) by 21 days.

(21) Appl. No.: 10/215,420

(22) Filed: Aug. 8, 2002

(65) Prior Publication Data

US 2003/0034407 A1 Feb. 20, 2003

Related U.S. Application Data

(60) Provisional application No. 60/312,182, filed on Aug. 14, 2001.

(51) Int. Cl.[7] ................................................. B05B 5/00
(52) U.S. Cl. ..................................... 239/696; 239/690.1
(58) Field of Search ............................... 239/590.5, 589, 239/690.1, 696, 704, 706

(56) References Cited

U.S. PATENT DOCUMENTS

| | | | | |
|---|---|---|---|---|
| 3,848,635 A | * | 11/1974 | Scheffler, Jr. ............... 137/872 |
| 5,423,489 A | * | 6/1995 | Wood ......................... 239/575 |
| 5,518,182 A | * | 5/1996 | Sasao ......................... 239/412 |
| 5,685,482 A | * | 11/1997 | Sickles ......................... 239/3 |
| 5,992,453 A | * | 11/1999 | Zimmer .................... 137/561 A |
| 6,263,918 B1 | * | 7/2001 | Lewis et al. ................ 137/597 |
| 2002/0063176 A1 | * | 5/2002 | Leuteritz et al. ............ 239/696 |

* cited by examiner

*Primary Examiner*—Thomas Denion
*Assistant Examiner*—Diem Tran
(74) *Attorney, Agent, or Firm*—Weingarten, Schurgin, Gagnebin & Lebovici LLP

(57) ABSTRACT

The present invention is directed to a flow splitter that includes an outer fluid conduit for receiving an incoming fluid flow that is the bulk flow of effluent from a liquid chromatographic column, flowing at an input flow rate. The flow splitter further includes an inner fluid conduit coaxially mounted within the outer fluid conduit so that a portion of the incoming fluid is split off into the inner fluid conduit and flows into the input end thereof. The inner fluid conduit extends beyond the exterior of the outer fluid conduit to provide an output fluid flow having an output flow rate that is less than the input flow rate. The outer fluid conduit further includes a fluid outlet that provides an outlet for the portion of the incoming fluid that is not split by the inner fluid conduit. A restriction valve can be coupled to the fluid outlet to finely adjust the output flow rate. The input end of the inner fluid conduit is positioned so as to be substantially free of turbulence from the fluid outlet.

12 Claims, 2 Drawing Sheets

FLUID NANOSPLITTER DEVICE

CROSS REFERENCE TO RELATED APPLICATIONS

The present application claims priority under 35 USC §119(e) of U.S. Provisional Application No. 60/312,182 titled Modular Microelectrospray System filed, Aug. 14, 2001.

STATEMENT REGARDING FEDERALLY SPONSORED RESEARCH OR DEVELOPMENT

The work leading to this invention was carried out with United States Government support provided under a grant from the National Institutes of Health, Grant No. R01 CA69390. Therefore, the United States Government has certain rights in this invention.

BACKGROUND OF THE INVENTION

The present invention is related to post chromatographic column fluid flow and in particular to a fluid splitting device to provide an interface between the liquid chromatographic column and the subsequent detection and analysis equipment.

High performance liquid chromatography-mass spectrometry (LC-MS) is a widely applied technique with a capacity for fast and sensitive characterization and quantification of pharmaceutical compounds and their metabolites. The analysis of these agents in complex biological fluids such as plasma, urine, bile and tissue homogenates, for the determination of pharmacokinetic parameters and metabolic pathways is a crucial step in the drug development process. The inherent specificity of mass detection coupled with the compound separation afforded by liquid chromatography has contributed to increased analytical productivity in the area of quantitative analysis by reducing the need for extensive sample preparation. In addition, the unique combination of detection sensitivity and information content has made LC-MS an essential tool in the determination of metabolic pathways. Such tools have resulted in reduced assay development times, reduced analysis times, and improved detection limits. Currently, several thousand quantitative assays can be carried out in a single day through the use of 96, 384 and higher well plate technology and tandem mass spectrometric (MS-MS) techniques. Furthermore, development in software applications has enabled the automated quantitative and qualitative characterization of drugs and metabolites, thus alleviating the bottleneck in data processing generated by increased sample throughput. The use of LC-MS based methodologies has become popular and widespread in the pharmaceutical industry. While these analytical techniques have provided outstanding results in recent years, there have been other problems associated with them.

For example, efforts to increase sample throughput have placed huge demands on analytical instrumentation to obtain near error-free measurements over long periods of time. In many instances, matrix components present in these samples are responsible for analysis failures and errors. These matrix components foul instrumentation and interfere with the detection process in mass spectrometry. Because ion transmission through the MS analyzer generally depends upon mass and mass-to-charge ratios and not on analyte structural features, problems with analyte detection have often been attributed to processes in the electrospray ionization region of the mass spectrometer, such as ionization suppression by the matrix components. Although the mechanism by which matrix components suppress the analyte signal is not fully understood, many components in biological fluids, such as salts, bile acids and other compounds, may exist in very large relative abundance to the desired analyte. These components also may have very high ionization efficiencies (which will mask the desired analyte signal) or high surface activities that can reduce the analyte response and compromise the quality of the analytical measurements. In some cases, matrix components can cause ionization suppression to such an extent that major metabolites are rendered undetectable by MS.

These problems have resulted in the need for time-consuming sample preparation methods in order to remove a portion of the matrix components. However, such methods are often inadequate. For example, solid phase extraction methods are only moderately successful at limiting suppression effects since they rely on large differences in chromatographic behavior for matrix removal. Matrix components that remain following solid phase extraction cleanup typically have chromatographic behavior similar to that of the analytes. As a result, these components are likely to coelute with the analyte in LC-MS and continue to cause ion suppression and inaccurate composition results in MS.

It has been shown that reducing the electrospray ion flow rate down to the nanoliter per minute range leads to improvements in desolvation, ionization and ion transfer efficiencies over conventional electrospray ionization flows. In order to exploit these lower flow benefits, it becomes necessary to either utilize capillary columns or split the effluent from a large bore chromatographic column before it enters the mass spectrometer. The use of capillary columns suffers from many limitations, including lower mass loading and contamination due to matrix components which can lead to rapid deterioration in column performance. Larger diameter columns do not suffer from such drawbacks and as such offer more rugged and reproducible separations. Therefore, in order to take advantage of the benefits of each stage of an LC-MS analysis, an integrated system would require the effluent from a large bore LC column be split so that a reduced flow rate is introduced into the MS. A common technique used to reduce the flow rate of the column effluent is the use of a "T" configuration fluid divider. Typically, in these dividers the effluent enters from one side and exits through the two outflow dividers. The ratio of the output flow rates is determined by the outflow dividers' flow resistances. These flow rates may be finely adjusted by providing a restriction valve on one arm of the divider. By adjusting the restriction valve, backpressure can be increased or decreased to adjust the flow rate of the other output arm. These dividers, however, tend to reduce the sensitivity and resolution of the chromatographic analysis due to band broadening caused by turbulence and/or mixing at the "split point" within the divider. In addition, current splitting devices contain a relatively large fluid volume between the fluid split point and the detection device. In general, the larger the volume introduced in the fluid path, the larger the impact on the chromatographic bands due to broadening.

Therefore, it would be advantageous to provide a fluid splitter or divider system that can be coupled to a standard size chromatographic column and in which turbulence at the split point has been minimized.

BRIEF SUMMARY OF THE INVENTION

The present invention is directed to a fluid splitting device that provides an accurate output fluid flow rate in which the turbulence and mixing at the split point are substantially minimized. A fluid flow splitting device in accordance with the present invention includes an outer fluid conduit that has first and second ends, an exterior surface, a fluid inlet coupled to the incoming fluid and a fluid outlet spaced apart from the fluid inlet. The fluid splitting device further includes an inner fluid conduit that is coaxially disposed within the outer fluid conduit. The inner fluid conduit has a fluid input end in fluid communication with the fluid inlet of the outer fluid conduit, wherein the fluid input end forms a fluid split point at which a portion of the input fluid is diverted so that it flows into the inner fluid conduit. The inner fluid conduit also has an output end that extends beyond the exterior surface of the outer fluid conduit and provides an output fluid flow at an output fluid flow rate, which directly interfaces with the detection method. Advantageously, this minimizes the extra-column effects by minimizing the fluid volume between the split point and the detector. The input end of the inner fluid conduit, i.e., the split point, is interposed between the fluid inlet and the fluid outlet of the outer fluid conduit. The positioning of the fluid split point away from the fluid outlet helps to ensure that the fluid input end of the inner fluid conduit is substantially free from turbulence from the fluid outlet. The portion of the incoming fluid that flows into the fluid input end of the inner fluid conduit forms the output fluid of the device and has a flow rate that is less than the input flow rate. Use of an inner fluid conduit of minimal volume (in the low nanoliter range) enables optimal chromatographic performance. The remaining input fluid leaves the outer fluid conduit via the fluid outlet as a waste fluid at a waste fluid flow rate. The output fluid flow rate can be adjusted by adjusting the relative dimensions of the inner and outer fluid conduit. If desired, a variable flow resistor such as a restriction valve or a predetermined length of fluid conduit having a predetermined flow resistance can be coupled to the fluid outlet of the outer fluid conduit and used to adjust the waste fluid flow rate, thereby adjusting the output fluid flow rate.

Other features, aspects, and advantages of the present invention will be apparent from the Detailed Description of the Invention in conjunction with the drawing.

BRIEF DESCRIPTION OF THE DRAWINGS

The present invention will be more fully understood by reference to the following Detailed Description of the Invention in conjunction with the Drawings of which.

DETAILED DESCRIPTION OF THE INVENTION

The U.S. Provisional Application No. 60/312,182 titled Modular Microelectrospray System filed, Aug. 14, 2001, is hereby incorporated by reference.

The present invention is directed to a flow splitter for receiving and diverting a portion of an incoming fluid flow, which typically is the bulk flow of effluent from a liquid chromatographic column and is flowing at an input flow rate. The flow splitter further includes an inner fluid conduit coaxially disposed within the outer fluid conduit so that a portion of the incoming fluid is split off or diverted at a split point into the input end of the inner fluid conduit. An output end of the inner fluid conduit extends beyond the exterior of the outer fluid conduit and directly provides an output fluid flow e.g., to an analytical detector such as a mass spectrometer or other detection device. The output fluid has an output flow rate that is less than the input flow rate. The outer fluid conduit further includes a fluid outlet that provides a waste fluid path for the portion of the incoming fluid that is not diverted by the inner fluid conduit. The waste fluid path also provides an additional means of recovering analytes as desired via fraction collection. If desired, a restriction valve may be coupled to the fluid outlet to adjust the flow resistance of the waste fluid path. As will be explained in more detail below, the output flow rate is a function of the ratio of the flow resistances of the waste fluid path and the output fluid path. Accordingly, by adjusting the flow resistance in the waste fluid path, the ratio of the flow resistances can be set and the output flow rate adjusted to a desired value. The input end of the inner fluid conduit is positioned within the outer fluid conduit so that the fluid split point is substantially free of turbulence from the fluid outlet.

Figure 1:
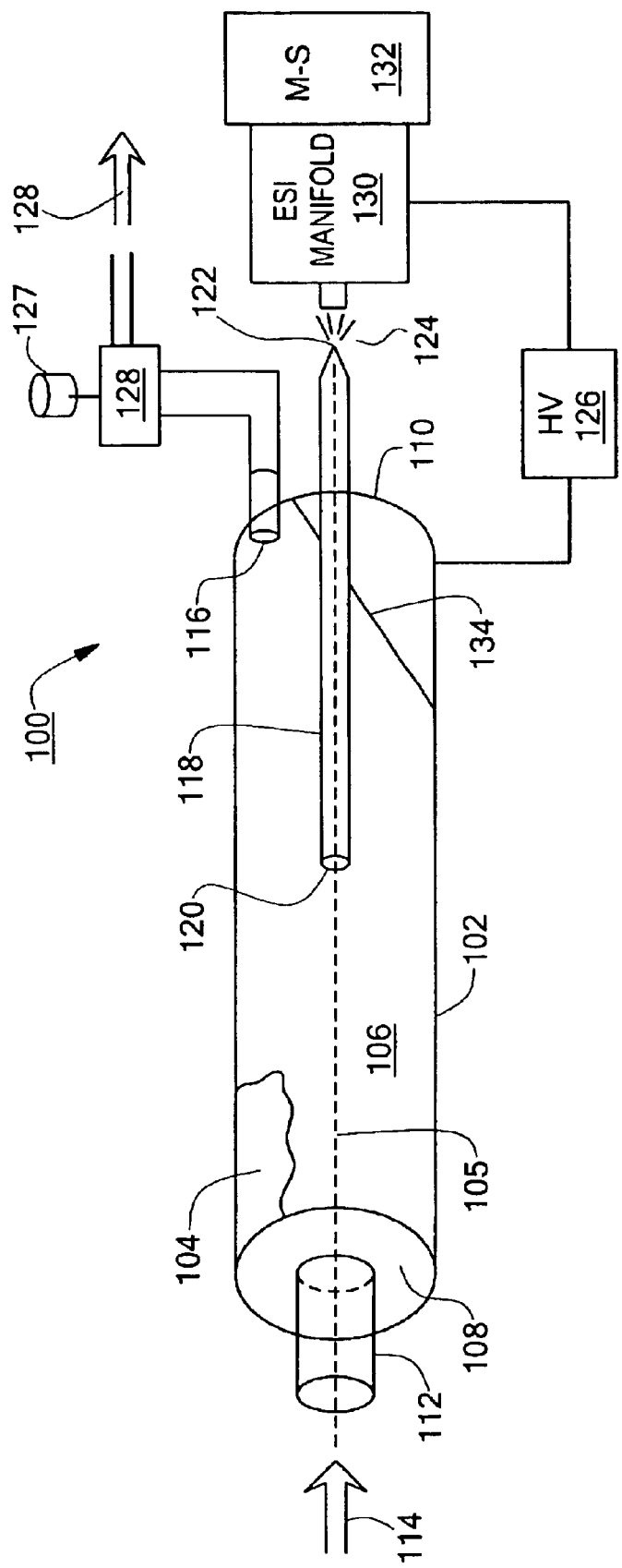
FIG. 1 is a block diagram of a fluid splitting apparatus in accordance with the present invention.

FIG. 1 depicts one embodiment of a fluid splitter 100 in accordance with the present invention. The fluid splitter 100 includes an outer fluid conduit 102 that includes an exterior shell 104 surrounding an interior 106, a first end 108, a second end 110, fluid inlet 112, and a fluid outlet 116. The fluid inlet 112 receives an incoming fluid 114 at an incoming flow rate and directs the incoming fluid into the interior 106 of the outer fluid conduit 102. The fluid outlet 116 allows waste fluid, i.e., fluid that is not diverted into the inner fluid conduit 118, to leave the outer fluid conduit 102 at a waste flow rate. The fluid splitter further includes an inner fluid conduit 118 disposed coaxially within the interior 106 of the outer fluid conduit 102. The inner fluid conduit includes a fluid input end 120 and an output end 122. The fluid input end 120 is coaxially disposed within the interior 106 of the outer fluid conduit 102, and the output end 122 extends through the exterior shell 104 to provide an output fluid 124 at an output flow rate. The input end 120 of the inner fluid conduit 118 forms the fluid split point, that is, the point at which a portion of the input fluid is split off (or diverted) from the input fluid and caused to flow into the inner fluid conduit 118. As used herein, coaxially means that the inner fluid conduit 108 is concentric with the outer fluid conduit 102 and shares a common longitudinal axis 105.

Figure 2:
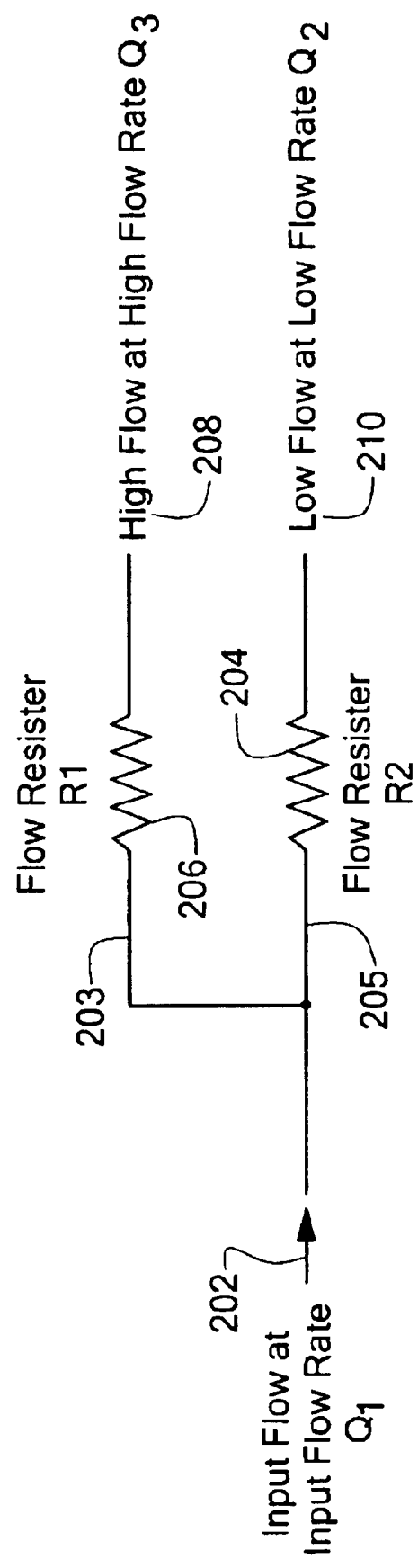
FIG. 2 is a schematic diagram of the fluid paths and corresponding fluid resistances of the fluid splitter depicted in FIG. 1.

FIG. 2 depicts a schematic of the fluid splitter 100 in terms of flow paths and the flow resistance in each path. The input flow rate Q1, 202 is provided to two fluid paths: a first path 203 includes a fluid flow resistor R1, 206, that incorporates the fluid flow resistance of the outer fluid conduit 102 and the fluid resistance of the waste fluid path including the fluid outlet 116 and a restriction valve if used. The second path 205 includes a fluid resistance R2, 204 that incorporates the fluid flow resistance of a portion of the outer fluid conduit 102 and the fluid flow resistance of the inner fluid conduit 118. The input flow rate and the ratio of the flow resistances in each of the two fluid paths R1 and R2 determine the flow rate in the two fluid paths Q1 and Q2 respectively. In this embodiment, the fluid resistance of the inner fluid conduit, R2, is greater than the fluid resistance R1 such that the waste flow rate, Q3, is greater than the output flow rate, Q2.

In general, the flow resistance of a tube or capillary is proportional to the length of the tube or capillary and inversely proportional to the diameter of the tube or capillary raised to the fourth power. Accordingly, the ratio of the waste flow rate to the output flow rate can be set by adjusting respective flow resistance of the two fluid paths: that is, the output flow rate may be set by adjusting the ratio of the lengths and the diameters of the two fluid conduits.

Adjusting the length and diameter of the capillaries as described above, under ideal conditions, can achieve the desired output flow rate. However, inaccuracies in manufacture, unknown and undesirable matrix components, and other externalities can result in the fluid resistances of either or both of the two fluid paths diverging from their desired values, resulting in an output flow rate that is not the desired value. These deviatons in the flow rates can result in decreased accuracy and reproducibility of the analytical result. In order to achieve a fine level of control over the ratio of the fluid resistances and hence the value of the output flow rate, the embodiment depicted in FIG. 1 includes a variable flow resistance device 126 placed in fluid communication with the fluid outlet 116 and in the waste fluid path. By adjusting the waste fluid flow through the variable flow resistance device 128, the fluid resistance of the waste fluid path can be adjusted, and the ratio of the waste fluid flow resistance to the output fluid flow resistance may be accurately set.

In the illustrated embodiment, the variable flow resistance device 128 is a restriction valve and in particular is a needle type valve. Other types of single port and multiport valves may be used as well. In addition, electronic feedback control systems can be used to monitor the various flow rates in the splitter and automatically adjust the flow resistance of the restriction valve to provide the desired flow rates. Other forms of variable flow resistance devices may be used. For example, a predetermined length of capillary having a predetermined diameter and flow resistance can be coupled to the fluid outlet 116.

Referring again to FIG. 1, as discussed above, the inner fluid conduit 118 is disposed coaxially within the outer fluid conduit 102. In this configuration, the fluid input end 120 of the inner fluid conduit 118 samples the incoming fluid 114 from the center and a small area surrounding the center of the outer fluid conduit 102. In a liquid chromatographic effluent, due to the fluid resistance of the walls of the chromatographic column, the bands of separated components travel the column in somewhat of a "U" shaped orientation, where the bottom of the U is nearly centered in the column and is pointed in the direction of fluid flow. If the incoming fluid is sampled from substantially the center of the column, the flat part of the chromatographic band is the portion that is sampled. This sampling of the flat area of the chromatographic band results in less band dispersion and spreading. Thus, the coaxial placement of the inner fluid conduit 118 allows for sharper and more defined bands to be sampled.

The normal flow of the input fluid into the interior 106 of the outer fluid conduit 102 should be as smooth and turbulent free as possible to avoid mixing the effluent and broadening the chromatographic bands. As discussed above, band spreading in the effluent of a chromatographic column deleteriously affects the chromatographic integrity (resolution) and detection accuracy of the analysis. Additionally, the waste fluid flowing out of the outer fluid conduit 102 via fluid outlet 116 produces turbulence in the chromatographic effluent. In addition, if a variable flow resistance device 126 is also used, the turbulence problem is further exacerbated. To reduce the turbulence caused by the waste fluid flow, the second end 110 includes a sloping surface 130 having a central bore to allow the inner fluid conduit 118 to pass through. The sloping surface 130 smoothly directs the waste fluid to the fluid outlet 116 that is disposed in the second end 110 of the outer fluid conduit 102.

In the illustrated embodiment, the outer and inner fluid conduits 102 and 118 are cylindrical in shape. The outer fluid conduit has an inner diameter of 700–4000 $\mu$m, the inner fluid conduit has an outside diameter of 150–500 $\mu$m, an inside diameter of 10–100 $\mu$m, and the output end has an inside diameter of 2–20 $\mu$m. The various combinations of dimensions that are used in the inner fluid conduit 118 allows various configurations of the fluid splitting device described herein. In particular, the amount of the fluid volume inserted between the chromatographic column and the detection device can be optimized according to other system requirements. In the illustrated embodiment, the amount of fluid volume inserted between the split point (inner fluid conduit input end 120) and the detection device is less than 100 nL, and ideally less than 50 nL. In this illustrated embodiment, the input flow rate is between 0.040 mL/min and 5 mL/min and the output fluid flow rate is between 20 nL/min and 500 nL/min. This corresponds to split ratios between the input fluid flow rate and the output fluid flow rate of between 500:1 and 10,000:1.

To limit the effects of the turbulence and mixing on the chromatographic bands, the fluid split point, i.e., the fluid input end 120 of the inner fluid conduit 118, is interposed between the fluid inlet 112 and the fluid outlet 116. The fluid split point is the point within the outer fluid conduit 102 at which a portion of the input fluid flow is split off and is sampled by the inner fluid conduit 118. The input end 120 is placed an appropriate distance from the fluid outlet 116 to minimize the effect of turbulence from the fluid outlet 116 on the sampled input fluid.

In the embodiment depicted in FIG. 1, the flow splitter 100 can also be configured as an integrated fluid slitter and electrospray ionization (ESI) system to provide both a fluid splitting and an ESI interface to a mass spectrometer. In particular, the output end 122 is tapered to a narrower diameter than the input end 120 of the inner fluid conduit 118, forming a nozzle. A high voltage supply 126 is utilized to ionize the droplets of the output fluid and is electrically connected to the outer fluid conduit 102 and the ESI manifold 130 of the mass spectrometer 132. In a preferred embodiment in which the flow splitter 100 is used as an ESI interface, the outer shell of the outer fluid conduit is made of stainless steel, and the inner fluid conduit is made from fused silica. In this embodiment, the inner fluid conduit is in fluid communication with the input fluid and provides electrical contact between the input fluid and an electrical ground at the electrospray manifold. Normal safety precautions should be taken to prevent electrical shocks in this embodiment. Advantageously, this integrated configuration minimizes the extra-column effects by minimizing the fluid volume contained between the split point and the mass spectrometer. In this embodiment, it is conceivable that electroosmotic flow contributes to preserving the chromatographic integrity of the bands, in accordance with the flattened plug profile generated by electroosmotic flow.

It will be appreciated by those of ordinary skill in the art that modifications to and variations of the above-described fluid splitting device may be made without departing from the inventive concepts disclosed herein. Accordingly, the invention should not be viewed as limited except by the scope and spirit of the appended claims.

What is claimed is:

1. An integrated fluid splitting device and electrospray ionization interface for receiving an incoming fluid having an input fluid flow rate and for diverting a portion of said incoming fluid to form an output fluid having an output fluid flow rate, and for vaporizing and ionizing said output fluid, said fluid splitting and electrospray ionization device comprising:

an outer fluid conduit having first and second ends an exterior surface, and a fluid inlet, said fluid inlet being in fluid communication with said incoming fluid, said outer fluid conduit further including a fluid outlet spaced apart from said fluid inlet; and an inner fluid conduit coaxially disposed within said outer fluid conduit, said inner fluid conduit having a fluid input end in fluid communication with said fluid inlet of said outer fluid conduit and a nozzle end extending beyond said exterior surface of said outer fluid conduit, said nozzle end providing said output fluid flow at said output fluid flow rate, wherein said fluid input end of said inner fluid conduit forms a fluid split point that is interposed between said fluid inlet and fluid outlet of said outer fluid conduit such that said fluid split point is substantially free from turbulence and mixing from said fluid outlet, and wherein a portion of said incoming fluid entering said outer fluid conduit flows into said fluid input end of said inner fluid conduit and is thereby split from said input fluid to form said output fluid and wherein said output fluid flow rate is less than said input fluid flow rate, and wherein said remaining input fluid leaves said outer fluid conduit via said fluid outlet as a waste fluid at a waste fluid flow rate; and wherein said outer fluid conduit is an electrical conductor and said inner fluid conduit is fused silica, and further including an electrical connection between said outer fluid conduit and a high voltage source.

2. The fluid splitting and electrospray ionization device of claim 1 further comprising a variable flow resistance device coupled to said fluid outlet and fluid communication therewith, said variable flow resistance device being operational to adjust said waste fluid flow rate and thereby adjust said output fluid flow rate.

3. The fluid splitting and electrospray ionization device of claim 2 wherein the variable flow resistance device is a restriction valve.

4. The fluid splitting and electrospray ionization device of claim 3 wherein the restriction valve is a needle valve.

5. The fluid splitting and electrospray ionization device of claim 2 wherein the variable flow resistance device is a predetermined length of fluid conduit having a predetermined diameter and a predetermined flow resistance.

6. The fluid splitting and electrospray ionization device of claim 1 wherein a fluid split ratio between the input flow rate and the output flow rate is between 500:1 and 10,000:1.

7. The fluid splitting and electrospray ionization device of claim 6 wherein said input fluid flow rate is between 0.040 mL/min and 5 mL/min and said output fluid flow rate is between 20 nL/min and 500 nL/min.

8. The fluid splitting and electrospray ionization device of claim 1 wherein said fluid outlet is disposed at said second end of said outer fluid conduit.

9. The fluid splitting and electrospray ionization device of claim 1 wherein said inner fluid conduit has an outside diameter of 150–500 $\mu$m, an inside diameter of 10–100 $\mu$m, and said output end has an inside diameter of 2–20 $\mu$m.

10. The fluid splitting and electrospray ionization device of claim 8 wherein the inner fluid conduit contributes a fluid volume less than 100 nL.

11. The fluid splitting and electrospray ionization device of claim 8 wherein the inner fluid conduit contributes a fluid volume less than 50 nL.

12. The fluid splitting and electrospray ionization device of claim 1 wherein the outer fluid conduit further includes a sloping surface to direct waste fluid to said fluid outlet.

* * * * *

UNITED STATES PATENT AND TRADEMARK OFFICE
CERTIFICATE OF CORRECTION

| | | |
|---|---|---|
| PATENT NO. | : 6,817,554 B2 | Page 1 of 1 |
| APPLICATION NO. | : 10/215420 | |
| DATED | : November 16, 2004 | |
| INVENTOR(S) | : Eric Gangl et al. | |

It is certified that error appears in the above-identified patent and that said Letters Patent is hereby corrected as shown below:

Column 5, line 8, "deviatons" should read --deviations--; and

Column 6, line 30, "slitter" should read --splitter--.

Signed and Sealed this

Fifth Day of December, 2006

JON W. DUDAS
*Director of the United States Patent and Trademark Office*